(12) United States Patent
Williams

(10) Patent No.: US 10,881,359 B2
(45) Date of Patent: Jan. 5, 2021

(54) COMPUTED TOMOGRAPHY SYSTEM FOR IMAGING MULTIPLE ANATOMICAL TARGETS

(71) Applicant: Hologic, Inc., Marlborough, MA (US)

(72) Inventor: Cornell Lee Williams, North East, MD (US)

(73) Assignee: HOLOGIC, INC., Marlborough, MA (US)

( * ) Notice: Subject to any disclaimer, the term of this patent is extended or adjusted under 35 U.S.C. 154(b) by 177 days.

(21) Appl. No.: 16/106,472

(22) Filed: Aug. 21, 2018

(65) Prior Publication Data

US 2019/0059830 A1 Feb. 28, 2019

Related U.S. Application Data

(60) Provisional application No. 62/548,804, filed on Aug. 22, 2017.

(51) Int. Cl.
*A61B 6/03* (2006.01)
*A61B 6/00* (2006.01)
(Continued)

(52) U.S. Cl.
CPC ............ *A61B 6/032* (2013.01); *A61B 6/4014* (2013.01); *A61B 6/4435* (2013.01); *A61B 6/482* (2013.01);
(Continued)

(58) Field of Classification Search
CPC .. A61B 6/032; A61B 6/54; A61B 6/50; A61B 6/4435; A61B 6/502; A61B 6/4014;
(Continued)

(56) References Cited

U.S. PATENT DOCUMENTS 3,365,575 A 1/1968 Strax
3,502,878 A 3/1970 Stewart
(Continued)

FOREIGN PATENT DOCUMENTS

DE 102004051401 5/2006
DE 102004051820 A1 5/2006
(Continued)

OTHER PUBLICATIONS

European Search Report in Application 18189199.5, dated Feb. 1, 2019, 7 pages.
(Continued)

*Primary Examiner* — David P Porta
*Assistant Examiner* — Gisselle M Gutierrez

(57) ABSTRACT

Methods and systems for imaging anatomical portions of a patient. A method includes moving a radiation source and a detector at least partially around a longitudinal axis of the patient, emitting radiation at a first energy level at a first angle around a longitudinal axis of the patient, wherein the first energy level is a predetermined energy level for a first anatomical target, detecting the radiation emitted at the first energy level, emitting radiation at a second energy level at second angle around the longitudinal axis of the patient, wherein the second energy level is a predetermined energy level for a second anatomical target; and detecting the radiation emitted at the second energy level. The method may be performed with a standing CT machine.

17 Claims, 11 Drawing Sheets

(51) Int. Cl.
　　　*A61B 6/02*　　　　　(2006.01)
　　　*G01N 23/046*　　　(2018.01)
(52) U.S. Cl.
　　　CPC .............. *A61B 6/50* (2013.01); *A61B 6/502*
　　　　　(2013.01); *A61B 6/54* (2013.01); *A61B 6/027*
　　　　　(2013.01); *A61B 6/4064* (2013.01); *A61B*
　　　　　*6/466* (2013.01); *A61B 6/5235* (2013.01);
　　　　　*G01N 23/046* (2013.01); *G01N 2223/419*
　　　　　(2013.01)
(58) Field of Classification Search
　　　CPC ......... A61B 6/482; A61B 6/027; A61B 6/466;
　　　　　A61B 6/4064; A61B 6/5235; G01M
　　　　　11/0285; G01M 11/005; B07C 5/342;
　　　　　G01N 21/958; G01N 2223/419; G01N
　　　　　23/046
　　　USPC ...................................................... 250/341.8
　　　See application file for complete search history.

(56) References Cited

U.S. PATENT DOCUMENTS

| | | | |
|---|---|---|---|
| 3,863,073 A | 1/1975 | Wagner |
| 3,971,950 A | 7/1976 | Evans et al. |
| 4,160,906 A | 7/1979 | Daniels et al. |
| 4,310,766 A | 1/1982 | Finkenzeller et al. |
| 4,380,086 A | 4/1983 | Vagi |
| 4,496,557 A | 1/1985 | Malen et al. |
| 4,513,433 A | 4/1985 | Weiss et al. |
| 4,542,521 A | 9/1985 | Hahn et al. |
| 4,559,641 A | 12/1985 | Caugant et al. |
| 4,662,379 A | 5/1987 | Macovski |
| 4,706,269 A | 11/1987 | Reina et al. |
| 4,721,856 A | 1/1988 | Saotome et al. |
| 4,744,099 A | 5/1988 | Huettenrauch et al. |
| 4,752,948 A | 6/1988 | MacMahon |
| 4,760,589 A | 7/1988 | Siczek |
| 4,763,343 A | 8/1988 | Yanaki |
| 4,773,086 A | 9/1988 | Fujita et al. |
| 4,773,087 A | 9/1988 | Plewes |
| 4,819,258 A | 4/1989 | Kleinman et al. |
| 4,821,727 A | 4/1989 | Levene et al. |
| 4,969,174 A | 11/1990 | Scheid et al. |
| 4,989,227 A | 1/1991 | Tirelli et al. |
| 4,998,270 A | 3/1991 | Scheid et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,142,557 A | 8/1992 | Toker |
| 5,163,075 A | 11/1992 | Lubinsky et al. |
| 5,164,976 A | 11/1992 | Scheid et al. |
| 5,199,056 A | 3/1993 | Darrah |
| 5,212,637 A | 5/1993 | Saxena |
| 5,240,011 A | 8/1993 | Assa |
| 5,256,370 A | 10/1993 | Slattery et al. |
| 5,274,690 A | 12/1993 | Burke |
| 5,289,520 A | 2/1994 | Pellegrino et al. |
| 5,291,539 A | 3/1994 | Thumann et al. |
| 5,313,510 A | 5/1994 | Ebersberger |
| 5,359,637 A | 10/1994 | Webber |
| 5,365,562 A | 11/1994 | Toker |
| 5,415,169 A | 5/1995 | Siczek et al. |
| 5,426,685 A | 6/1995 | Pellegrino et al. |
| 5,452,367 A | 9/1995 | Bick et al. |
| 5,506,877 A | 4/1996 | Niklason et al. |
| 5,526,394 A | 6/1996 | Siczek et al. |
| 5,528,658 A | 6/1996 | Hell |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzke et al. |
| 5,609,152 A | 3/1997 | Pellegrino et al. |
| 5,627,869 A | 5/1997 | Andrew et al. |
| 5,657,362 A | 8/1997 | Giger et al. |
| 5,668,844 A | 9/1997 | Webber |
| 5,668,889 A | 9/1997 | Hara |
| 5,706,327 A | 1/1998 | Adamkowski et al. |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,841,829 A | 11/1998 | Dolazza |
| 5,844,965 A | 12/1998 | Galkin |
| 5,864,146 A | 1/1999 | Karellas |
| 5,872,828 A | 2/1999 | Niklason et al. |
| 5,878,104 A | 3/1999 | Ploetz |
| 5,896,437 A | 4/1999 | Ploetz |
| 5,941,832 A | 8/1999 | Tumey et al. |
| 5,970,118 A | 10/1999 | Sokolov |
| 5,983,123 A | 11/1999 | Shmulewitz |
| 5,986,662 A | 11/1999 | Argiro et al. |
| 5,999,836 A | 12/1999 | Nelson et al. |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers et al. |
| 6,137,527 A | 10/2000 | Abdel-Malek et al. |
| 6,141,398 A | 10/2000 | He et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,207,958 B1 | 3/2001 | Giakos |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,244,507 B1 | 6/2001 | Garland |
| 6,256,369 B1 | 7/2001 | Lai |
| 6,256,370 B1 | 7/2001 | Yavuz |
| 6,272,207 B1 | 8/2001 | Tang |
| 6,289,235 B1 | 9/2001 | Webber et al. |
| 6,292,530 B1 | 9/2001 | Yavus et al. |
| 6,327,336 B1 | 12/2001 | Gingold et al. |
| 6,341,156 B1 | 1/2002 | Baetz et al. |
| 6,345,194 B1 | 2/2002 | Nelson et al. |
| 6,375,352 B1 | 4/2002 | Hewes et al. |
| 6,411,836 B1 | 6/2002 | Patel et al. |
| 6,415,015 B2 | 7/2002 | Nicolas et al. |
| 6,418,189 B1 * | 7/2002 | Schafer .............. G01N 23/046 |
| | | 378/57 |
| 6,442,288 B1 | 8/2002 | Haerer et al. |
| 6,459,925 B1 | 10/2002 | Nields et al. |
| 6,480,565 B1 | 11/2002 | Ning |
| 6,490,476 B1 | 12/2002 | Townsend et al. |
| 6,501,819 B2 | 12/2002 | Unger et al. |
| 6,542,575 B1 | 4/2003 | Schubert |
| 6,553,096 B1 | 4/2003 | Zhou et al. |
| 6,556,655 B1 | 4/2003 | Chichereau et al. |
| 6,574,304 B1 | 6/2003 | Hsieh et al. |
| 6,574,629 B1 | 6/2003 | Cooke, Jr. et al. |
| 6,597,762 B1 | 7/2003 | Ferrant et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,744,848 B2 | 6/2004 | Stanton et al. |
| 6,748,044 B2 | 6/2004 | Sabol et al. |
| 6,751,285 B2 | 6/2004 | Eberhard et al. |
| 6,758,824 B1 | 7/2004 | Miller et al. |
| 6,813,334 B2 | 11/2004 | Koppe et al. |
| 6,882,700 B2 | 4/2005 | Wang et al. |
| 6,885,724 B2 | 4/2005 | Li et al. |
| 6,895,076 B2 | 5/2005 | Halsmer |
| 6,909,790 B2 | 6/2005 | Tumey et al. |
| 6,909,792 B1 | 6/2005 | Carrott et al. |
| 6,912,319 B1 | 6/2005 | Barnes et al. |

(56) References Cited

U.S. PATENT DOCUMENTS

| | | |
|---|---|---|
| 6,940,943 B2 | 9/2005 | Claus et al. |
| 6,950,493 B2 | 9/2005 | Besson |
| 6,957,099 B1 | 10/2005 | Arnone et al. |
| 6,970,531 B2 | 11/2005 | Eberhard et al. |
| 6,978,040 B2 | 12/2005 | Berestov |
| 6,987,831 B2 | 1/2006 | Ning |
| 6,999,554 B2 | 2/2006 | Mertelmeier |
| 7,001,071 B2 | 2/2006 | Deuringer |
| 7,016,461 B2 | 3/2006 | Rotondo |
| 7,110,490 B2 | 9/2006 | Eberhard et al. |
| 7,110,502 B2 | 9/2006 | Tsuji |
| 7,116,749 B2 | 10/2006 | Besson |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,190,758 B2 | 3/2007 | Hagiwara |
| 7,206,462 B1 * | 4/2007 | Betke .......... G06T 7/0012 378/21 |
| 7,244,063 B2 | 7/2007 | Eberhard |
| 7,245,694 B2 | 7/2007 | Jing et al. |
| 7,286,645 B2 | 10/2007 | Freudenberger |
| 7,302,031 B2 | 11/2007 | Hjarn et al. |
| 7,315,607 B2 | 1/2008 | Ramsauer |
| 7,319,734 B2 | 1/2008 | Besson |
| 7,319,735 B2 | 1/2008 | Defreitas et al. |
| 7,319,736 B2 | 1/2008 | Rotondo |
| 7,323,692 B2 | 1/2008 | Rowlands et al. |
| 7,331,264 B2 | 2/2008 | Ozawa |
| 7,430,272 B2 | 9/2008 | Jing et al. |
| 7,443,949 B2 | 10/2008 | Defreitas et al. |
| 7,577,282 B2 | 8/2009 | Gkanatsios et al. |
| 7,583,786 B2 | 9/2009 | Jing et al. |
| 7,609,806 B2 | 10/2009 | Defreitas et al. |
| 7,616,731 B2 | 11/2009 | Pack |
| 7,616,801 B2 | 11/2009 | Gkanatsios et al. |
| 7,630,531 B2 | 12/2009 | Chui |
| 7,630,533 B2 | 12/2009 | Ruth et al. |
| 7,688,940 B2 | 3/2010 | Defreitas et al. |
| 7,697,660 B2 | 4/2010 | Ning |
| 7,702,142 B2 | 4/2010 | Ren et al. |
| 7,760,853 B2 | 7/2010 | Jing et al. |
| 7,760,924 B2 | 7/2010 | Ruth et al. |
| 7,792,245 B2 | 9/2010 | Hitzke et al. |
| 7,831,296 B2 | 11/2010 | Defreitas et al. |
| 7,839,979 B2 | 11/2010 | Hauttmann |
| 7,869,563 B2 | 1/2011 | Defreitas et al. |
| 7,881,428 B2 | 2/2011 | Jing et al. |
| 7,885,384 B2 | 2/2011 | Mannar |
| 7,894,646 B2 | 2/2011 | Shirahata et al. |
| 7,916,915 B2 | 3/2011 | Gkanatsios et al. |
| 7,949,091 B2 | 5/2011 | Jing et al. |
| 7,986,765 B2 | 7/2011 | Defreitas et al. |
| 7,991,106 B2 | 8/2011 | Ren et al. |
| 8,031,834 B2 | 10/2011 | Ludwig |
| 8,131,049 B2 | 3/2012 | Ruth et al. |
| 8,155,421 B2 | 4/2012 | Ren et al. |
| 8,170,320 B2 | 5/2012 | Smith et al. |
| 8,175,219 B2 | 5/2012 | Defreitas et al. |
| 8,285,020 B2 | 10/2012 | Gkanatsios et al. |
| 8,416,915 B2 | 4/2013 | Jing et al. |
| 8,452,379 B2 | 5/2013 | DeFreitas et al. |
| 8,457,282 B2 | 6/2013 | Baorui et al. |
| 8,515,005 B2 | 8/2013 | Ren et al. |
| 8,559,595 B2 | 10/2013 | Defreitas et al. |
| 8,565,372 B2 | 10/2013 | Stein et al. |
| 8,565,374 B2 | 10/2013 | DeFreitas et al. |
| 8,565,860 B2 * | 10/2013 | Kimchy .......... A61B 5/055 250/363.01 |
| 8,571,289 B2 | 10/2013 | Ruth et al. |
| 8,712,127 B2 | 4/2014 | Ren et al. |
| 8,767,911 B2 | 7/2014 | Ren et al. |
| 8,787,522 B2 | 7/2014 | Smith et al. |
| 8,831,171 B2 | 9/2014 | Jing et al. |
| 8,853,635 B2 * | 10/2014 | O'Connor .......... A61B 6/037 250/363.01 |
| 8,873,716 B2 | 10/2014 | Ren et al. |
| 9,042,612 B2 | 5/2015 | Gkanatsios et al. |
| 9,066,706 B2 | 6/2015 | Defreitas et al. |
| 9,226,721 B2 | 1/2016 | Ren et al. |
| 9,460,508 B2 | 10/2016 | Gkanatsios et al. |
| 9,498,175 B2 | 11/2016 | Stein et al. |
| 9,502,148 B2 | 11/2016 | Ren |
| 9,549,709 B2 | 1/2017 | DeFreitas et al. |
| 9,851,888 B2 | 12/2017 | Gkanatsios et al. |
| 9,895,115 B2 | 2/2018 | Ren |
| 10,108,329 B2 | 10/2018 | Gkanatsios et al. |
| 10,194,875 B2 | 2/2019 | DeFreitas et al. |
| 10,296,199 B2 | 5/2019 | Gkanatsios |
| 10,413,255 B2 | 9/2019 | Stein |
| 10,452,252 B2 | 10/2019 | Gkanatsios et al. |
| 10,638,994 B2 | 5/2020 | DeFreitas |
| 10,719,223 B2 | 7/2020 | Gkanatsios |
| 2001/0038681 A1 | 11/2001 | Stanton et al. |
| 2002/0012450 A1 | 1/2002 | Tsujii |
| 2002/0048343 A1 | 4/2002 | Launay et al. |
| 2002/0050986 A1 | 5/2002 | Inouc et al. |
| 2002/0070970 A1 | 6/2002 | Wood et al. |
| 2002/0075997 A1 | 6/2002 | Unger et al. |
| 2002/0090055 A1 | 7/2002 | Zur et al. |
| 2002/0094062 A1 * | 7/2002 | Dolazza .......... G01N 23/04 378/98.9 |
| 2002/0122533 A1 | 9/2002 | Marie et al. |
| 2002/0126798 A1 | 9/2002 | Harris |
| 2003/0007598 A1 | 1/2003 | Wang et al. |
| 2003/0018272 A1 | 1/2003 | Treado et al. |
| 2003/0026386 A1 | 2/2003 | Tang et al. |
| 2003/0058989 A1 | 3/2003 | Rotondo |
| 2003/0072409 A1 | 4/2003 | Kaufhold et al. |
| 2003/0072417 A1 | 4/2003 | Kaufhold et al. |
| 2003/0073895 A1 | 4/2003 | Nields et al. |
| 2003/0095624 A1 | 5/2003 | Eberhard et al. |
| 2003/0097055 A1 | 5/2003 | Yanof et al. |
| 2003/0169847 A1 | 9/2003 | Karellas et al. |
| 2003/0194050 A1 | 10/2003 | Eberhard |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0212327 A1 | 11/2003 | Wang et al. |
| 2003/0215120 A1 | 11/2003 | Uppaluri et al. |
| 2004/0008809 A1 | 1/2004 | Webber |
| 2004/0066882 A1 | 4/2004 | Eberhard et al. |
| 2004/0066884 A1 | 4/2004 | Hermann Claus et al. |
| 2004/0066904 A1 | 4/2004 | Eberhard et al. |
| 2004/0070582 A1 | 4/2004 | Smith et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0146221 A1 | 7/2004 | Siegel et al. |
| 2004/0171986 A1 | 9/2004 | Tremaglio, Jr. et al. |
| 2004/0190682 A1 | 9/2004 | Deuringer |
| 2004/0213378 A1 | 10/2004 | Zhou et al. |
| 2004/0247081 A1 | 12/2004 | Halsmer |
| 2004/0264627 A1 | 12/2004 | Besson |
| 2004/0267157 A1 | 12/2004 | Miller et al. |
| 2005/0025278 A1 | 2/2005 | Hagiwara |
| 2005/0049521 A1 | 3/2005 | Miller et al. |
| 2005/0063509 A1 | 3/2005 | DeFreitas et al. |
| 2005/0078797 A1 | 4/2005 | Danielsson et al. |
| 2005/0105679 A1 | 5/2005 | Wu et al. |
| 2005/0113681 A1 | 5/2005 | DeFreitas et al. |
| 2005/0113715 A1 | 5/2005 | Schwindt et al. |
| 2005/0117694 A1 | 6/2005 | Francke |
| 2005/0129172 A1 | 6/2005 | Mertelmeier |
| 2005/0133706 A1 | 6/2005 | Eberhard |
| 2005/0135555 A1 | 6/2005 | Claus et al. |
| 2005/0135664 A1 | 6/2005 | Kaufhold et al. |
| 2005/0226375 A1 | 10/2005 | Eberhard et al. |
| 2005/0248347 A1 * | 11/2005 | Damadian .......... G01R 33/381 324/318 |
| 2006/0030784 A1 | 2/2006 | Miller et al. |
| 2006/0034426 A1 | 2/2006 | Freudenberger |
| 2006/0074288 A1 | 4/2006 | Kelly |
| 2006/0098855 A1 | 5/2006 | Gkanatsios et al. |

(56) References Cited

U.S. PATENT DOCUMENTS

| | | |
|---|---|---|
| 2006/0109951 A1* | 5/2006 | Popescu ................. A61B 6/032 378/4 |
| 2006/0126780 A1 | 6/2006 | Rotondo |
| 2006/0129062 A1 | 6/2006 | Nicoson et al. |
| 2006/0155209 A1 | 7/2006 | Miller et al. |
| 2006/0210016 A1 | 9/2006 | Francke |
| 2006/0262898 A1* | 11/2006 | Partain ................... A61B 6/502 378/37 |
| 2006/0269041 A1 | 11/2006 | Mertelmeier |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0076844 A1 | 4/2007 | Defreitas et al. |
| 2007/0078335 A1 | 4/2007 | Horn |
| 2007/0140419 A1 | 6/2007 | Souchay |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0045833 A1 | 2/2008 | Defreitas et al. |
| 2008/0056436 A1 | 3/2008 | Pack |
| 2008/0101537 A1 | 5/2008 | Sendai |
| 2008/0112534 A1 | 5/2008 | Defreitas |
| 2008/0118023 A1 | 5/2008 | Besson |
| 2008/0130979 A1 | 6/2008 | Ren |
| 2008/0212861 A1 | 9/2008 | Durgan et al. |
| 2008/0285712 A1 | 11/2008 | Kopans |
| 2008/0317196 A1* | 12/2008 | Imai ....................... A61B 6/405 378/8 |
| 2009/0003519 A1 | 1/2009 | Defreitas et al. |
| 2009/0010384 A1 | 1/2009 | Jing et al. |
| 2009/0080594 A1 | 3/2009 | Brooks et al. |
| 2009/0080602 A1 | 3/2009 | Brooks et al. |
| 2009/0135997 A1 | 5/2009 | Defreitas et al. |
| 2009/0141859 A1 | 6/2009 | Gkanatsios et al. |
| 2009/0213987 A1 | 8/2009 | Stein et al. |
| 2009/0237924 A1 | 9/2009 | Ladewig |
| 2009/0238424 A1 | 9/2009 | Arakita et al. |
| 2009/0268865 A1 | 10/2009 | Ren et al. |
| 2009/0296882 A1 | 12/2009 | Gkanatsios |
| 2009/0304147 A1 | 12/2009 | Jing et al. |
| 2010/0020937 A1 | 1/2010 | Hautmann |
| 2010/0020938 A1 | 1/2010 | Koch |
| 2010/0034450 A1 | 2/2010 | Mertelmeier |
| 2010/0054400 A1 | 3/2010 | Ren |
| 2010/0086188 A1 | 4/2010 | Ruth |
| 2010/0091940 A1 | 4/2010 | Ludwig et al. |
| 2010/0150306 A1 | 6/2010 | Defreitas et al. |
| 2010/0189227 A1 | 7/2010 | Mannar |
| 2010/0195882 A1 | 8/2010 | Ren |
| 2010/0226475 A1 | 9/2010 | Smith |
| 2010/0290585 A1 | 11/2010 | Eliasson |
| 2010/0303202 A1 | 12/2010 | Ren |
| 2010/0313196 A1* | 12/2010 | De Atley ................. G06F 8/61 717/174 |
| 2011/0026667 A1 | 2/2011 | Poorter |
| 2011/0069809 A1 | 3/2011 | Defreitas et al. |
| 2011/0178389 A1 | 7/2011 | Kumar et al. |
| 2011/0188624 A1 | 8/2011 | Ren |
| 2011/0234630 A1 | 9/2011 | Batman et al. |
| 2011/0268246 A1 | 11/2011 | Dafni |
| 2012/0033868 A1 | 2/2012 | Ren |
| 2012/0051502 A1 | 3/2012 | Ohta et al. |
| 2012/0236987 A1* | 9/2012 | Ruimi .................... A61B 6/4028 378/19 |
| 2012/0238870 A1 | 9/2012 | Smith et al. |
| 2013/0028374 A1 | 1/2013 | Gkanatsios et al. |
| 2013/0211261 A1* | 8/2013 | Wang ................... A61B 6/5217 600/476 |
| 2013/0272494 A1 | 10/2013 | DeFreitas et al. |
| 2014/0044230 A1 | 2/2014 | Stein et al. |
| 2014/0044231 A1 | 2/2014 | Defreitas et al. |
| 2014/0086471 A1 | 3/2014 | Ruth et al. |
| 2014/0098935 A1 | 4/2014 | Defreitas et al. |
| 2014/0232752 A1 | 8/2014 | Ren et al. |
| 2014/0314198 A1 | 10/2014 | Ren et al. |
| 2014/0321607 A1 | 10/2014 | Smith et al. |
| 2014/0376690 A1 | 12/2014 | Jing et al. |
| 2015/0049859 A1 | 2/2015 | DeFreitas et al. |
| 2015/0160848 A1 | 6/2015 | Gkanatsios et al. |
| 2015/0310611 A1 | 10/2015 | Gkanatsios et al. |
| 2016/0106383 A1 | 4/2016 | Ren et al. |
| 2016/0220207 A1* | 8/2016 | Jouhikainen ......... A61B 6/4021 |
| 2016/0256125 A1 | 9/2016 | Smith et al. |
| 2016/0270742 A9 | 9/2016 | Stein et al. |
| 2016/0331339 A1* | 11/2016 | Guo ....................... A61B 6/505 |
| 2017/0024113 A1 | 1/2017 | Gkanatsios et al. |
| 2017/0128028 A1 | 5/2017 | DeFreitas et al. |
| 2017/0135650 A1 | 5/2017 | Stein et al. |
| 2017/0319167 A1* | 11/2017 | Goto .................... A61B 6/5205 |
| 2018/0130201 A1* | 5/2018 | Bernard ................. A61B 6/025 |
| 2018/0177476 A1 | 6/2018 | Jing et al. |
| 2018/0188937 A1 | 7/2018 | Gkanatsios et al. |
| 2018/0289347 A1 | 10/2018 | DeFreitas et al. |
| 2018/0344276 A1 | 12/2018 | DeFreitas et al. |
| 2019/0095087 A1 | 3/2019 | Gkanatsios et al. |
| 2019/0200942 A1 | 7/2019 | DeFreitas |
| 2019/0336794 A1* | 11/2019 | Li ........................ A61B 6/0457 |
| 2020/0012417 A1 | 1/2020 | Gkanatsios |
| 2020/0029927 A1* | 1/2020 | Wilson ................. A61B 5/4875 |
| 2020/0085393 A1 | 3/2020 | Zhang |

FOREIGN PATENT DOCUMENTS

| | | |
|---|---|---|
| DE | 102010027871 | 10/2011 |
| EP | 0775467 | 5/1997 |
| EP | 0982001 | 3/2000 |
| EP | 1028451 | 8/2000 |
| EP | 1428473 | 6/2004 |
| EP | 1759637 | 3/2007 |
| EP | 1569556 | 4/2012 |
| EP | 2732764 A1 | 5/2014 |
| EP | 2602743 | 11/2014 |
| EP | 2819145 | 12/2014 |
| EP | 3143935 A1 | 3/2017 |
| JP | 53151381 U | 11/1978 |
| JP | 2001-346786 | 12/2001 |
| JP | 2002219124 | 8/2002 |
| JP | 2006-231054 | 9/2006 |
| JP | 2007-50264 | 3/2007 |
| JP | 2007-521911 | 8/2007 |
| JP | 2007229269 | 9/2007 |
| JP | 2008-67933 | 3/2008 |
| JP | 2008086471 | 4/2008 |
| JP | 2009500048 | 1/2009 |
| WO | WO 90/05485 | 5/1990 |
| WO | WO 9803115 | 1/1998 |
| WO | WO 98/16903 | 4/1998 |
| WO | WO 00/51484 | 9/2000 |
| WO | WO 03/020114 | 3/2003 |
| WO | WO 03037046 | 5/2003 |
| WO | WO 2003/057564 | 7/2003 |
| WO | WO 2004/043535 | 5/2004 |
| WO | WO 2005/051197 | 6/2005 |
| WO | WO 2005/110230 | 11/2005 |
| WO | WO 2005/112767 | 12/2005 |
| WO | WO 2006/055830 | 5/2006 |
| WO | WO 2006/058160 | 6/2006 |
| WO | WO 2007/129244 | 11/2007 |
| WO | WO 2008072144 | 6/2008 |
| WO | WO 2009122328 | 10/2009 |
| WO | WO 2009/136349 | 11/2009 |
| WO | WO 2010/070554 | 6/2010 |
| WO | WO 2013/184213 | 12/2013 |

OTHER PUBLICATIONS

"Essentials for life: Senographe Essential Full-Field Digital Mammography system", GE Health-care Brochure, MM-0132-05.06-EN-US, 2006, 12 pgs.

(56) References Cited

OTHER PUBLICATIONS

"Filtered Back Projection," (Nygren) published May 8, 2007; URL:http://web.archive.org/web/19991010131715/http://www.owlnet.rice.edu/-.about.elec539/Projects97/cult/node2.html., 2 pgs.
"Lorad Selenia" Document B-BI-SEO US/Intl (May 2006) copyright Hologic 2006, 12 pgs.
Acrin website, located at https://www.acrin.org/PATIENTS/ABOUTIMAGINGEXAMSANDAGENTS/ABOUTMAMMOGRAPHYANDTOMOSYNTHESIS.aspx, "About Mammography and Tomosynthesis", obtained online on Dec. 8, 2015, 5 pgs.
American College of Radiology website, located at http://www.acr.org/FAQs/DBT-FAQ, "Digital Breast Tomosynthesis FAQ for Insurers", obtained online on Dec. 8, 2015, 2 pages.
Aslund, Magnus, "Digital Mammography with a Photon Counting Detector in a Scanned Multislit Geometry", Doctoral Thesis, Dept of Physics, Royal Institute of Technology, Stockholm, Sweden, Apr. 2007, 51 pages.
Chan, Heang-Ping et al., "ROC study of the effect of stereoscopic imaging on assessment of breast lesions", Medical Physics, vol. 32, No. 4, Apr. 2005, 7 pgs.
Cole, Elodia, et al., "The Effects of Gray Scale Image Processing on Digital Mammography Interpretation Performance", Academic Radiology, vol. 12, No. 5, pp. 585-595, May 2005.
Digital Clinical Reports, Tomosynthesis, GE Brochure 98-5493, Nov. 1998, 8 pgs.
Dobbins, James T., "Digital x-ray tomosynthesis: current state of the art and clinical potential," Physics in Medicine and Biology, Taylor and Francis LTD, London GB, vol. 48, No. 19, Oct. 7, 2003, 42 pages.
Grant, David G., "Tomosynthesis: a three-dimensional imaging technique", IEEE Trans. Biomed. Engineering, vol. BME-19, #1, Jan. 1972, pp. 20-28.
Japanese Office Action mailed in Application 2016-087710, dated Mar. 1, 2017, 5 pages.
Japanese Office Action mailed in Application 2017-001579, dated Mar. 29, 2017, 1 page. (No English Translation.).
Kachelriess, Marc et al., "Flying Focal Spot (FFS) in Cone-Beam CT", 2004 IEEE Nuclear Science Symposium Conference Record, Oct. 16-22, 2004, Rome Italy, vol. 6, pp. 3759-3763.
Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.
Mammographic Accreditation Phantom, http://www.cirsinc.com/pdfs/015cp.pdf. (2006), 2 pgs.
Niklason, Loren T. et al., "Digital Tomosynthesis in Breast Imaging", Radiology, Nov. 1997, vol. 205, No. 2, pp. 399-406.
Pediconi, Federica et al., "Color-coded automated signal intensity-curve for detection and characterization of breast lesions: Preliminary evaluation of a new software for MR-based breast imaging", International Congress Series 1281 (2005) 1081-1086.
Pisano, Etta D., "Digital Mammography", Radiology, vol. 234, No. 2, Feb. 2005, pp. 353-362.
Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.
Smith, A., "Fundamentals of Breast Tomosynthesis", White Paper, Hologic Inc., WP-00007, Jun. 2008, 8 pgs.
Smith, Andrew, PhD, "Full Field Breast Tomosynthesis", Hologic White Paper, Oct. 2004, 6 pgs.
Wheeler F. W., et al. "Micro-Calcification Detection in Digital Tomosynthesis Mammography", Proceedings of SPIE, Conf-Physics of Semiconductor Devices, Dec. 11, 2001 to Dec. 15, 2001, Delhi, SPIE, US, vol. 6144, Feb. 13, 2006, 12 pgs.
Wu, Tao, et al. "Tomographic Mammography Using a Limited Number of Low-Dose Cone-Beam Projection Images" Medical Physics, AIP, Melville, NY, vol. 30, No. 3, Mar. 1, 2003, p. 365-380.

\* cited by examiner

COMPUTED TOMOGRAPHY SYSTEM FOR IMAGING MULTIPLE ANATOMICAL TARGETS

CROSS-REFERENCE TO RELATED APPLICATION

This application claims priority to U.S. Provisional Application No. 62/548,804, titled "COMPUTED TOMOGRAPHY SYSTEM FOR IMAGING MULTIPLE ANATOMICAL TARGETS," filed on Aug. 22, 2017, the entire disclosure of which is hereby incorporated by reference in its entirety.

BACKGROUND

Patients and the healthcare system prefer not to have to undergo multiple scans to test for potential abnormalities, such as cancer, for different portions of the body. The need for multiple scans is not only time consuming and potentially uncomfortable for the patient, it may expose the patient to multiple and potentially unnecessary rounds of radiation. For breast cancer screening and diagnosis—one type of common scan—a common patient concern is the discomfort the patient may feel when the breast is compressed, typically between two rigid plastic surfaces, with sufficient force to immobilize the breast and spread out the breast tissues for x-ray imaging.

As an example, breast cancer and lung cancer are, unfortunately, often found together in patients. In some cases, breast cancer has formed first and metastasized to the lung. In other cases, lung cancer has formed first and metastasized to the breast. Currently, different tests are utilized to determine if a patient has breast cancer and/or lung cancer. For instance, a chest x-ray or mammogram may first be performed and analyzed. If the chest x-ray indicates potential cancer development, a computed tomography (CT) scan may be performed, followed by one or more of a positron emission tomography (PET) scan, a PET CT scan, a magnetic resonance imaging (MM) scan, and tomosynthesis scan, as well as maybe a follow up biopsy procedure. While not all of these scans may be used in every case, such a process is burdensome on the patient and healthcare system.

SUMMARY

In one aspect, the technology relates to a method for imaging two or more anatomical portions of a patient. The method includes moving a radiation source and a detector at least partially around a longitudinal axis of the patient; emitting radiation at a first energy level at a first angle around a longitudinal axis of the patient, wherein the first energy level is a predetermined energy level for a first anatomical target; detecting the radiation emitted at the first energy level; emitting radiation at a second energy level at second angle around the longitudinal axis of the patient, wherein the second energy level is a predetermined energy level for a second anatomical target; and detecting the radiation emitted at the second energy level. In an example, the first anatomical target is a breast and the second anatomical target is a lung. In another example, the first energy level is less than the second energy level. In yet another example, the energy levels of the radiation emitted from the radiation source are controlled by altering voltage across the radiation source. In still another example, the first energy level corresponds to a voltage of less than 50 kV across the radiation source and the second energy level corresponds to a voltage of 50 kV or greater across the radiation source. In still yet another example, the method further includes reconstructing the first anatomical target from the detected radiation emitted at the first energy level.

In another example the method further includes displaying a representation of the first anatomical target. In yet another example, the method further includes reconstructing the second anatomical target from the detected radiation emitted at the second energy level. In still another example, the method further includes displaying a representation of the second anatomical target. In still yet another example, the method further includes tracking movement of the first anatomical target based on at least one opaque marker placed on the first anatomical target.

In another example, tracking movement of the first anatomical target is based on at least one of heart pulses and breathing rates. In yet another example, the radiation source and the detector are housed within an annular housing defining a central aperture for a patient. In still another example, the annular housing is attached to a support structure extending substantially vertically from the ground, wherein the annular housing is configured to move around a patient in a standing position. In still yet another example, the emission and detection all occurs within a single scan spanning less than or equal to 360 degrees around the longitudinal axis of the patient.

In another aspect, the technology relates to a system for imaging anatomical portions of a human body. The system includes at least one support structure, wherein the support structure extends in an upwards direction from the ground; a gantry attached to the at least one support structure and configured to move along the support structure, wherein the gantry comprises an annular housing defining an inner aperture to allow for the annular housing to pass over a patient. The annular housing includes a radiation source configured to move through the annular housing around the inner aperture; and a radiation detector disposed substantially on an opposite side of the aperture from the radiation source and configured to move through the annular housing to remain substantially on the opposite side of the aperture from the radiation source as the radiation source moves. The system also includes a control system having at least one processor and memory, wherein the memory stores instructions that when executed by the at least one processor perform a set of operations. The operations include cause the radiation source to emit radiation at a first energy level for a first angular range around the annular housing; and cause the radiation source to emit radiation at a second energy level for a second angular range around the annular housing. In an example, the first energy level is predetermined based on a first anatomical target and the second energy level is predetermined based on a second anatomical target. In another example, the first anatomical target is a breast and the second anatomical target is a lung. In yet another example, the system further comprises a display screen for displaying a representation of the first anatomical target based on the radiation emitted at the first energy level and a representation of the second anatomical target based on the radiation emitted at the second energy level. In still another example, the first angular range is based on a position of the first anatomical target and the second angular range is based on a position of the second anatomical target. In still yet another example, the system also includes hand supports configured to allow a patient to grip the hand supports during scanning of the patient.

In another example, the emission of radiation all occurs within a single scan spanning less than or equal to 360 degrees around a longitudinal axis of a patient being scanned. In yet another example, the system further comprises a breast tray for supporting the at least one of the breasts of the patient during scanning.

In another aspect, the technology relates to a method for imaging anatomical portions of a patient. The method includes moving a gantry, having an annular housing with an aperture, down over a patient in a standing position such that the patient is within the aperture of the annular housing; moving a radiation source and a detector around the annular housing, such that the radiation source and the detector remain substantially opposite one another; while moving the radiation source around the annular housing, alternating radiation emission between a low-energy radiation and a high-energy radiation, wherein the low-energy radiation is predetermined based on a first anatomical target and the high-energy radiation is based on a second anatomical target; detecting the emitted radiation; and based on the emitted radiation, reconstructing the first anatomical target and the second anatomical target This summary is provided to introduce a selection of concepts in a simplified form that are further described below in the Detailed Description. This summary is not intended to identify key features or essential features of the claimed subject matter, nor is it intended to be used to limit the scope of the claimed subject matter.

DETAILED DESCRIPTION

The present technology relates to computed tomography (CT) systems that are capable of imaging multiple anatomical targets, such a breast and a lung, in a single scan of the patient. The CT systems disclosed herein utilize multiple energies of radiation during a single scan to allow for reconstruction of multiple anatomical targets of the patient, such as a breast and a lung. By doing so, the present technology reduces the number and types of scans that a patient may need to undergo. By reducing the number of scans experienced by the patient, the burden and radiation exposure to the patient are both reduced. In addition, by utilizing multiple energies of radiation, the overall dose of radiation may be considered to be low in comparison to a regular CT scan. In addition, once a patient is positioned, multiple scans may be performed for different segments of the body, such as the thorax and the abdomen. Indeed, the whole body may be scanned once the patient is positioned. Further, by using such technology, detection of abnormalities, such as cancer, that have spread or metastasized to other portions of the body can potentially be detected earlier. The use of the CT systems disclosed herein also eliminate the need for painful compression of the breast as is conventionally done in mammography, while still producing diagnostically relevant or useful images of the breast. Reduction in the number of scans also provides benefits to healthcare system, including imaging centers or hospitals, by providing higher patient throughput.

In addition, the CT systems disclosed herein include a standing, or upright, CT system. The standing CT system allows a patient to stand while a gantry is lowered over the patient and a scan is performed. The gantry is then raised after the scan, and the patient can exit. The standing CT system may make the patient feel more comfortable than a standard supine CT system that utilizes a moving bed. Further, the standing CT system takes up a smaller footprint of floor space, allowing for CT systems to be installed in smaller spaces or rooms, such as in a medical suite or hospital.

Figure 1A:
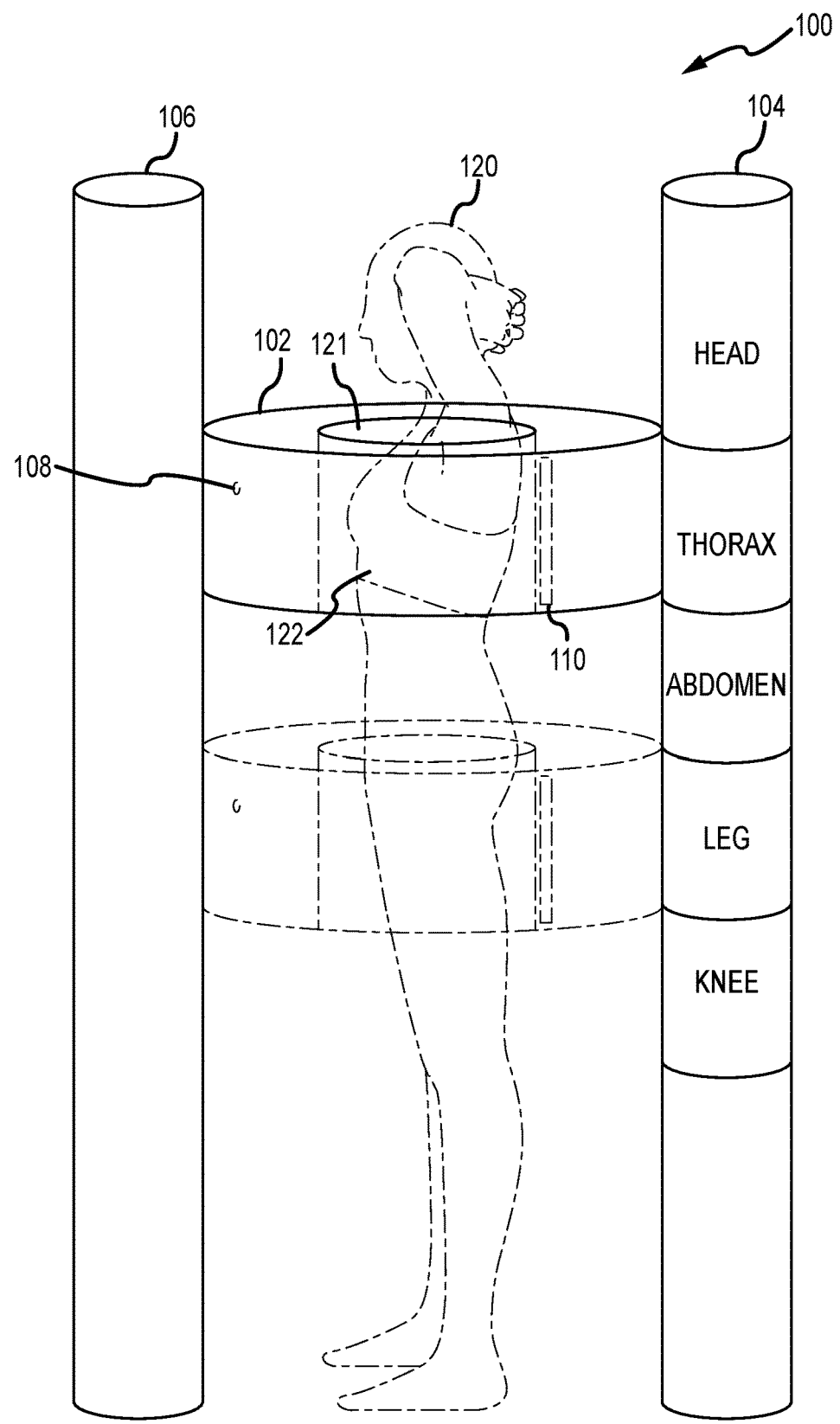
FIG. 1A depicts a side view of an example standing computed tomography (CT) system.

FIGS. 1A-1F depict different views and components of multiple example CT systems. For ease of reference, like components are labeled with like reference numerals. More specifically, FIG. 1A depicts a side view of an example standing computed tomography (CT) system 100. The standing CT system 100 includes a gantry 102 attached to one or more support structures, such support structure 104 and support structure 106. The gantry 102 includes a radiation source 108 and a radiation detector 110. The radiation source 108 may be an x-ray emission source, such as an x-ray tube. The radiation detector 110 may be any type of detector that is capable of detecting the radiation emitted from the radiation source 108. For example, the radiation detector 110 may be a flat panel, image plate, curved detector, or other type of detector having a plurality of pixels and capable of producing digital data signals representative of the detected radiation. The radiation source 108 and the radiation detector 110 may be housed and controlled within the gantry 102 such that they remain opposite one another during movement. In some examples, the components in the gantry 102 may be similar to that of a gantry of a standard supine CT system. For instance, the gantry 102 may include one or more filters, collimators, power sources, wiring, and internal support structures, among other components, that will be appreciated by those having skill in the art. As such, those components are not depicted in FIGS. 1A-1E or discussed in further detail herein.

The gantry 102 may include an annular housing that houses the radiation source 108 and the radiation detector 110. The gantry 102 is also attached to the one or more support structures, such as support structure 104 and support structure 106. While two support structures 104, 106 are depicted in FIG. 1A, a great or fewer number of support structures may be utilized to support the gantry 102. In the example standing CT system 100 depicted, the two support structures 104, 106 are disposed on substantially opposite sides of the gantry 102. Such a configuration of support structures 104, 106 allows for a patient 120 to more easily enter and exit the CT system. The gantry 102 is attached to the support structures 104, 106 in a manner that allows the gantry 102 to move along the support structures 104, 106 along a substantially vertical axis. The connection mechanism and controls for moving the gantry 102 may be any mechanisms known to those having skill in the art, including belts, motors, gears, tracks, and other components. Further, the standing CT system 100 may also include, or be connected to, a workstation or other computerized mechanism for processing the detected data and/or displaying images based on the processed data. The workstation may be connected physically or wirelessly to the gantry 102 or any other component of the standing CT system 100.

The annular housing of the gantry 102 includes a central aperture 121 for the patient 120. In practice, the patient 120 may first be positioned under the aperture 121 of the annular housing. The proper positioning may also include the patient 120 raising his or her arms to a position above the head, or in a position that will not be scanned. Once the patient 120 is properly positioned, the gantry 102 is lowered such that the aperture 121 of the gantry 102 moves over the patient 120. The gantry 102 is lowered to a desired scanning height. For example, the gantry 102 may be lowered to height that is equivalent to the patient's 120 head, thorax, abdomen, leg, knee, or any other desired scanning height. The scanning height is generally determined based on the anatomical targets of the patient 120 that are desired to be imaged. For example, if the breast and the lung are desired to be imaged, the gantry 102 is lowered to height equivalent to the thorax of the patient 120. Once the gantry 102 has been lowered, scanning commences, as discussed further below. Additional supports (not depicted) for the patient 120 may also be included that assist the patient 120 in stabilizing herself or himself once the gantry 102 has been lowered. For instance, hand holds may be included that help the patient 120 keep the arms of the patient 120 above the head of the patient 120. Other supports may extend from the ground to allow the patient 120 to a lean against a structure. The annular housing of the gantry 102 may also include an openable portion to allow for a patient 120 to enter the central aperture 121 of the gantry 102. For example, the gantry may include a sliding or hinged door, or another sliding or hinged portion, to allow patient 120 to enter without having to raise and lower the gantry 102.

If the patient 120 is female, the patient 120 may be provided a support bra 122 to wear during the scan. The support bra 122 may be configured to stabilize the breasts during the scan, without causing pain to the patient 120. The support bra 122 may also separate the breasts during the scan. By separating the breasts, the reconstruction of each individual breast may be more easily achieved. A non-compression breast tray (e.g., a tray upon which the breasts rest) that separates the breast may also be used in combination or in lieu of the support bra 122. In some examples, the breast tray may be substantially radiolucent, such as clear plastic tray. Use of such a tray is in contrast to systems that require compression of the breast between two breast compression surfaces. The tray may be configured to receive one or both breasts of the patient.

In some examples, one or more radiopaque markers may be attached directly to each breast to allow for tracking the movement of the breasts during the scan. For instance, a radiopaque sticker or marker may be adhesively attached to each breast. Thus, as the breast moves perhaps during a breathing pattern, the marker can be tracked and the resultant images may be adjusted based on the movement of the breast. In some examples, multiple markers may be used to better track movement. Additionally, a heart rate monitor may also be incorporated into the standing CT system 100 to track the times of the heart rate, which causes movement of the breast and other anatomical features of the patient 120. The resultant images may then also be adjusted for the tracked heart beats. A breathing rate monitor may also be incorporated into the standing CT system 100 to track patient 120 breathing rate. The resultant images may then also be adjusted for the tracked breathing rate.

Figure 1B:
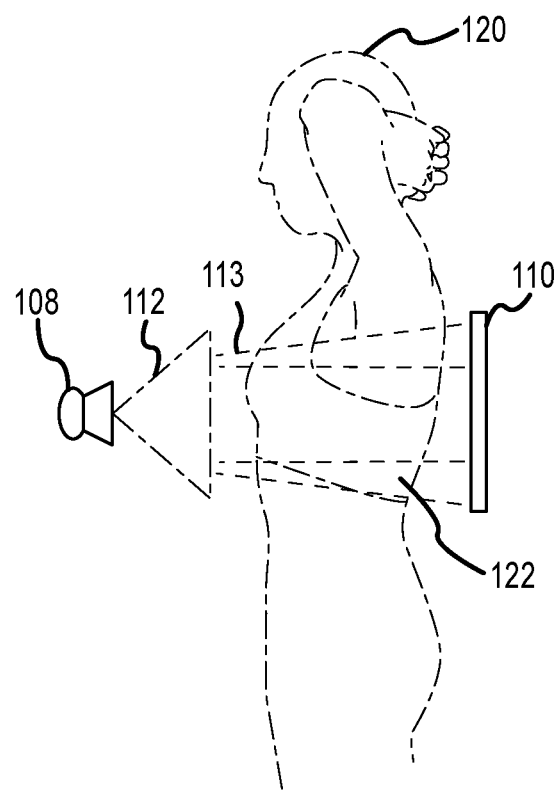
FIG. 1B depicts a view of components of the example standing CT system of FIG. 1A.

FIG. 1B depicts a view of components of the example standing CT system 100 of FIG. 1A. More specifically, FIG. 1B depicts the configuration of the radiation source 108 and the radiation detector 110 with respect to the patient 120. During a scan, the radiation source 108 emits radiation 112 through the patient 120. Once the radiation 112 passes through the patient 120, the radiation 112 is detected by the radiation detector 110. The radiation 112 may also be collimated prior to passing through the patient 120 to form collimated radiation 113. In addition, the radiation may be filtered prior to and/or after passing through the patient 120.

The energy of the radiation 112 that is emitted from the radiation source 108 may also be changed or altered during the scan. For instance, the radiation 112 emitted from the radiation source 108 may be switched from a high-energy radiation to a low-energy radiation. In an example where the radiation source 108 is an x-ray tube, the energy of the radiation emitted may be altered by changing the voltage across the x-ray tube. For example, low-energy radiation may be emitted when less than 50 kV is applied across the radiation source 108 and high-energy radiation may be emitted when 50 kV or more is applied across the radiation source 108. A high-energy radiation beam may be referred to as a "harder" beam than a low-energy beam. Conversely, a low-energy beam may be referred to as a "softer" beam than the high-energy radiation beam. A high-energy radiation beam may be desired where an anatomical target is located more internal to the body (e.g., a lung). The high-energy beam thus has enough energy to pass through the exterior of the body and other obstacles, such as a ribcage or heart, and still retain enough energy to allow for accurate imaging of the internal anatomical target. A low-energy radiation beam may be desired where an anatomical target is located closer to the exterior, such as an appendage or breast. In some examples, the particular energy level used may be further based on the specific anatomical target(s) selected for imaging. For instance, if a lung is to be imaged, a particular voltage may be applied across the radiation source 108. If a breast is to be imaged, a different particular voltage may be applied across the radiation source 108. The voltage may also be altered as the radiation source 108 moves to allow for imaging of multiple anatomical targets, as discussed in further detail below. The radiation detector 110 may be a broadband detector such that it can accurately detect the multiple energy levels of the emitted radiation. In some examples, filters may also be used in conjunction with the radiation detector 110 to allow the detection of multiple energy levels of radiation.

Figure 1C:
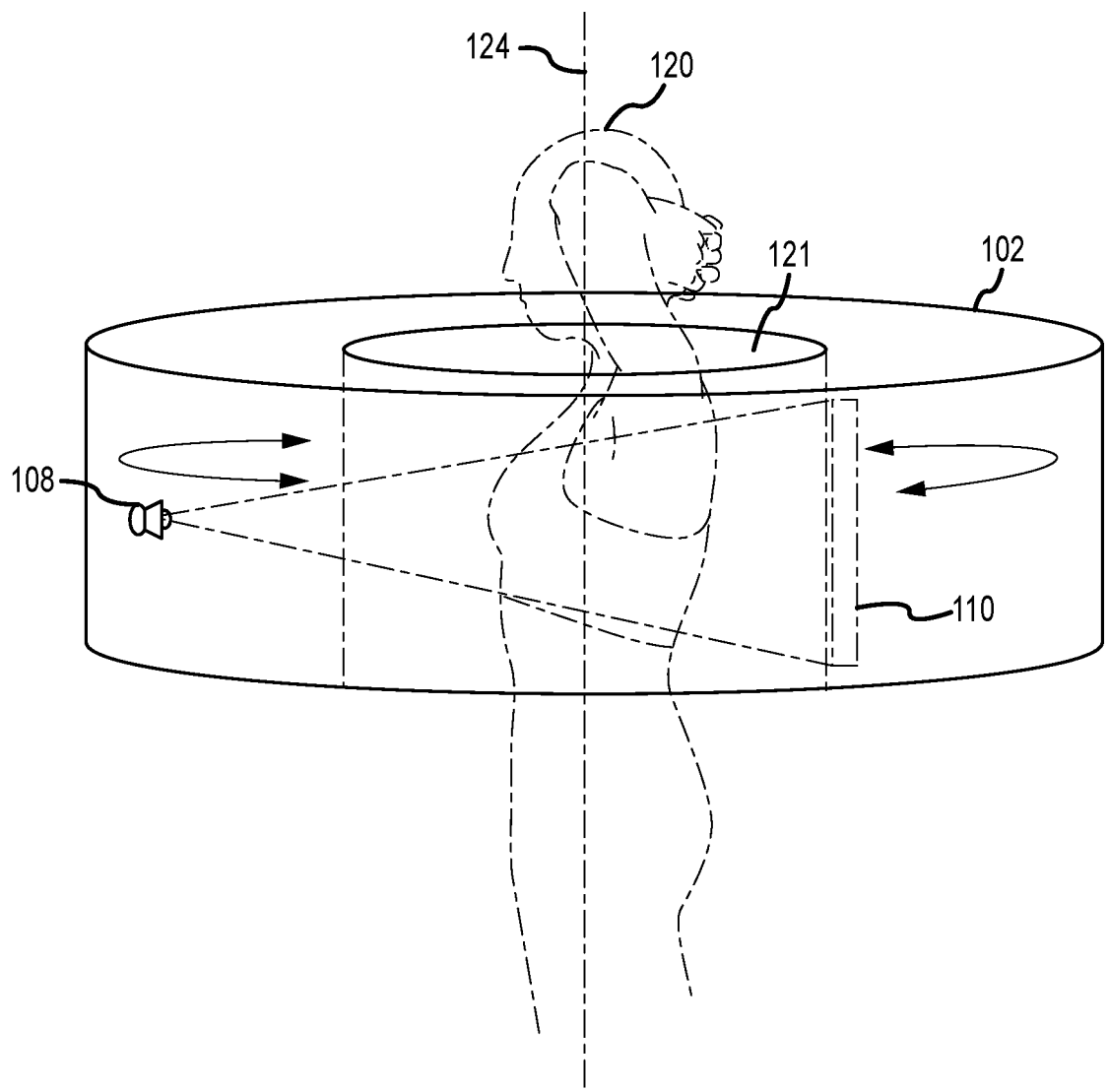
FIG. 1C depicts another view of components of the example standing CT system of FIG. 1A.

FIG. 1C depicts another view of components of the example standing CT system 100 of FIG. 1A. More specifically, FIG. 1C depicts the radiation source 108 and the radiation detector 110 within the annular housing of the gantry 102. The radiation source 108 and radiation detector 110 are disposed on substantially opposite sides of the patient 120. The radiation source 108 and the radiation detector 110 may move around a longitudinal axis 124 of the patient 120 through the housing of the gantry 102. As the radiation source 108 and the detector 110 move throughout the annular housing, they remain on substantially opposite sides of the patient 120 so as to allow for the radiation emitted by the radiation source 108 to be detected by the detector 110 after passing through the patient. As the radiation source 108 moves around the annular housing of the gantry 102, it may emit different energy levels of radiation 112 depending on the respective angle of the energy source with reference to the patient 120.

In other examples, multiple detectors may be incorporated into the annular housing. In such an example, the detectors may remain stationary while the radiation source moves. In other examples, multiple sources and multiple detectors may be utilized such that each radiation source may be activated as a sequence, and no physical movement of the sources is required. However, the same effect of the radiation source 108 moving may be achieved. In yet another example, a single large detector may be utilized to provide a similar result.

Figure 1D:
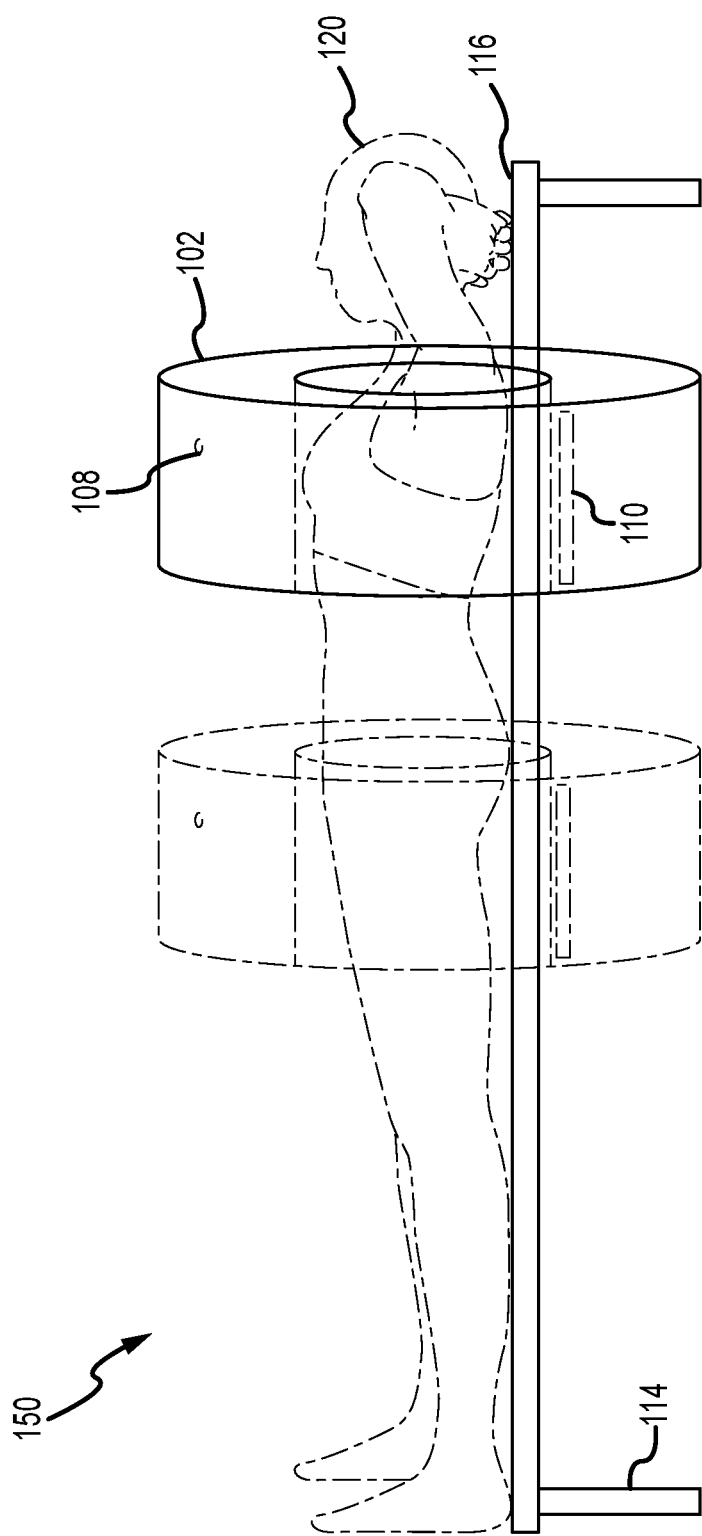
FIG. 1D depicts a side view of an example supine CT system.

FIG. 1D depicts a side view of an example supine CT system 150. The supine CT system is substantially similar to the standing CT system 100. However, the supine CT system 150 does not include the same support structures 104, 106 as the standing CT system 100. Rather, the supine CT system 150 includes a table or bed 116 with supports or legs 114. In some examples, the gantry 102 may still move relative to the table 116, but in other examples, the table 116 (or portions thereof) moves through the aperture of the gantry 102 and the gantry is fixed to the floor. In the supine CT system 150, the radiation source 108 and detector 110 still move around the longitudinal axis of the patient. In general, the supine CT system 150 has a larger footprint (e.g., takes up more floor space) than a standing CT system 100. Those having skill in the art will appreciate other features of a supine CT system 150.

Figure 1E:
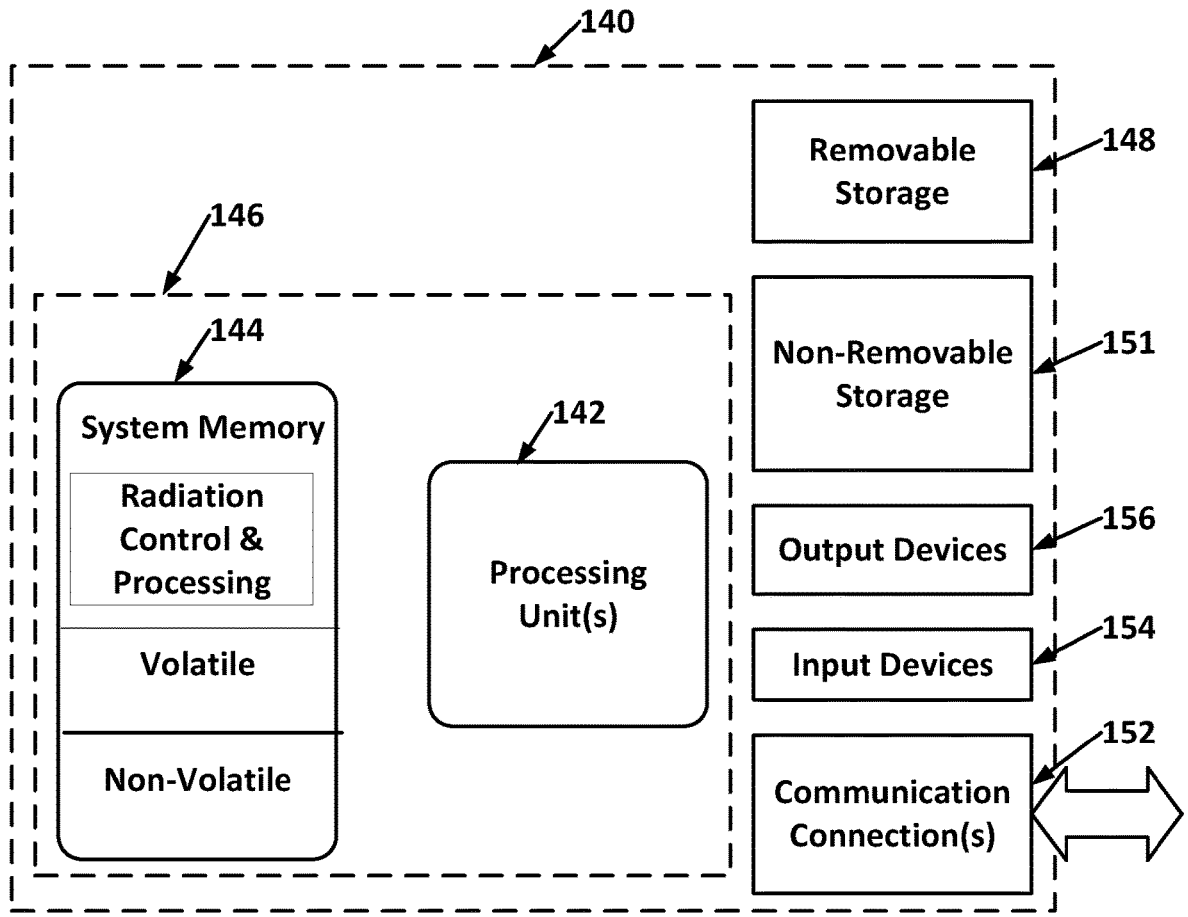
FIG. 1E depicts an example of a suitable operating environment for use with the present examples.

FIG. 1E depicts an example of a suitable operating environment 140 for use with the present examples. The computing device 140 is a suitable operating environment in which one or more of the present examples can be implemented. This operating environment may be incorporated directly into a scanning system, a workstation, or may be incorporated into a computer system discrete from, but used to control or process data from, the scanning systems described herein. This is only one example of a suitable operating environment and is not intended to suggest any limitation as to the scope of use or functionality. Other well-known computing systems, environments, and/or configurations that can be suitable for use include, but are not limited to, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 140 typically includes at least one processing unit 142 and memory 144. Depending on the exact configuration and type of computing device, memory 144 (storing, among other things, instructions to perform the measurement acquisition, processing, and visual representation generation methods disclosed herein) can be volatile (such as RAM), non-volatile (such as ROM, flash memory, etc.), or some combination of the two. This most basic configuration is illustrated in FIG. 1E by dashed line 146. Further, environment 140 can also include storage devices (removable, 148, and/or non-removable, 151) including, but not limited to, solid-state devices, magnetic or optical disks, or tape. Similarly, environment 140 can also have input device(s) 154 such as touch screens, keyboard, mouse, pen, voice input, etc., and/or output device(s) 156 such as a display, speakers, printer, etc. Also included in the environment can be one or more communication connections 152, such as LAN, WAN, point to point, Bluetooth, RF, etc.

Operating environment 140 typically includes at least some form of computer readable media. Computer readable media can be any available media that can be accessed by processing unit 142 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible and non-transitory medium which can be used to store the desired information.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 140 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in hospitals, offices, enterprise-wide computer networks, intranets and the Internet.

In some examples, the components described herein comprise such modules or instructions executable by computer system 140 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some examples, computer system 140 is part of a network that stores data in remote storage media for use by the computer system 140.

Figure 1F:
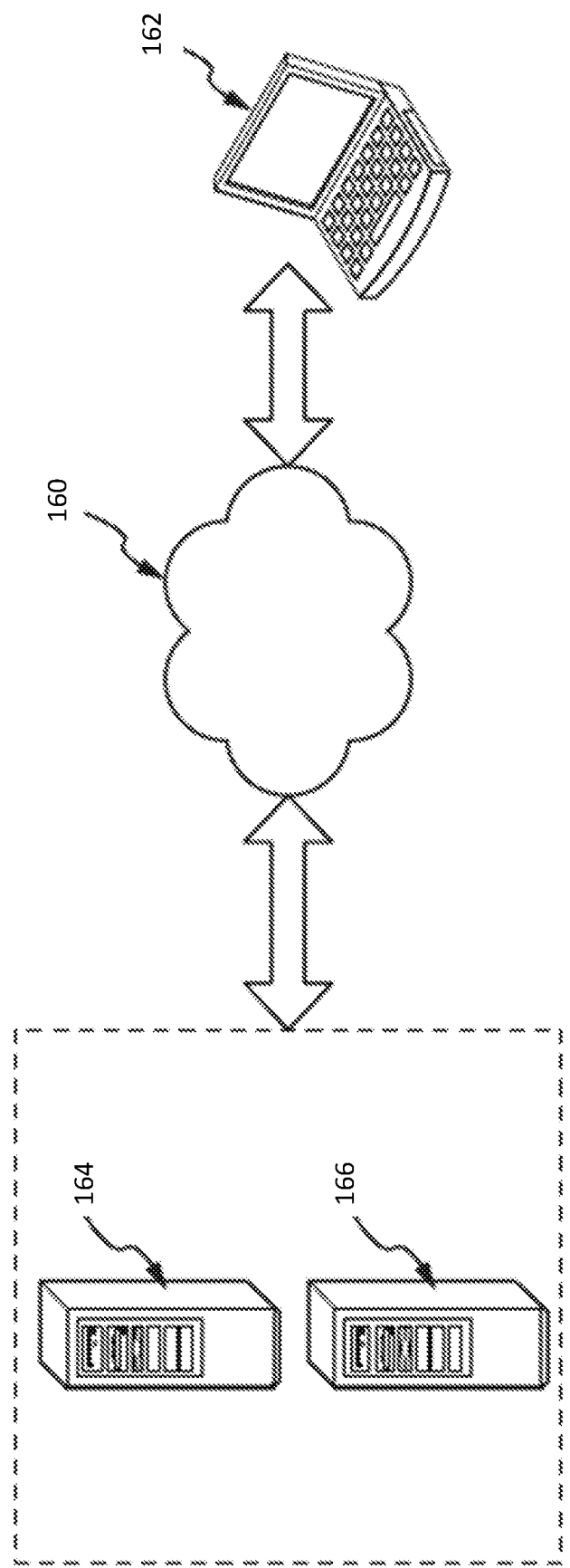
FIG. 1F depicts an example of a network in which the various systems and methods disclosed herein may operate.

FIG. 1F depicts an example of a network in which the various systems and methods disclosed herein may operate. In examples, a client device, such as client device 162, may communicate with one or more servers, such as servers 164 and 166, via a network 168. In examples, a client device may be a laptop, a personal computer, a smart phone, a PDA, a netbook, or any other type of computing device, such as the computing device in FIG. 1E. In examples, servers 164 and 166 may be any type of computing device, such as the computing device illustrated in FIG. 1E. Network 168 may be any type of network capable of facilitating communications between the client device and one or more servers 164 and 166. Examples of such networks include, but are not limited to, LANs, WANs, cellular networks, and/or the Internet.

In examples, processing of data and performance of the methods described herein may be accomplished with the use of one or more server devices. For example, in one example, a single server, such as server 164 may be employed to assist in processing data and performing the methods disclosed herein. Client device 162 may interact with server 164 via network 168. In further examples, the client device 162 may also perform functionality disclosed herein, such as scanning and processing data, which can then be provided to servers 164 and/or 166.

In alternate examples, the methods disclosed herein may be performed using a distributed computing network, or a cloud network. In such examples, the methods disclosed herein may be performed by two or more servers, such as servers 164 and 166. Although a particular network example is disclosed herein, one of skill in the art will appreciate that the systems and methods disclosed herein may be performed using other types of networks and/or network configurations. Further, the data sent to the servers and received from the servers may be encrypted. The data may also be stored in an encrypted manner both locally and on the servers.

Figure 2A:
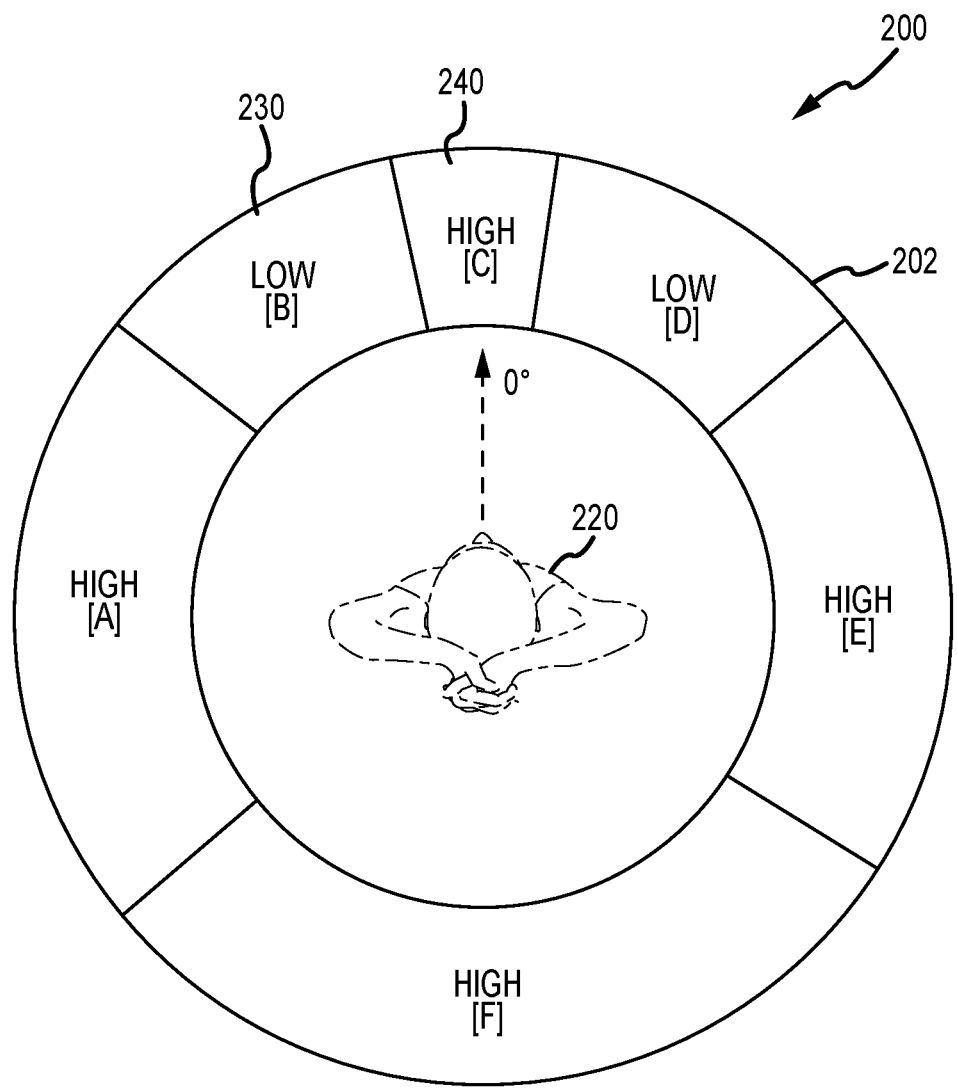
FIG. 2A depicts a view of an example CT system showing example regions of varying radiation emission.

FIG. 2A depicts a view of an example CT system 200 showing example regions of varying radiation emission. As a radiation source moves around a gantry 202, it may be controlled to emit varying energy levels of radiation. The radiation source may be controlled based on its relative angular location to the center of the aperture. For example, low-energy angular segments 230 and high-energy angular segments 240 may be used in controlling the radiation emission. As the radiation source passes through the low-energy segments 230, the radiation source emits low-energy radiation. As the radiation source passes through the high-energy segments 240, the radiation source emits high-energy radiation. While only two different types of angular segments (i.e., low energy and high energy) are depicted, other examples may include additional types of angular segments for different or intermediate energy levels. For example, if three or more anatomical targets are identified, three different types of angular segments may be utilized. Pre-scan information about the patient, as well as the starting point of the scan, modelled anatomy trajectory, and estimations based on previous scans of the patient or other patients may also be utilized in configuring the energy levels and angular segments.

The different angular segments may be defined by the angles that they encompass. As a reference point, the 0 degree angle may be defined as the angle perpendicular to the coronal plane in the anterior direction of the patient 220. For example, the angular segment [A] depicted in FIG. 2A may be defined as the angles from about 230 degrees to 310 degrees, the angular segment [B] may be defined as the angles from about 310 degrees to 350 degrees, the angular segment [C] may be defined as the angles from about 350 degrees to 10 degrees, the angular segment [D] may be defined as the angles from about 10 to 50 degrees, the angular segment [E] may be defined as the angles from about 50 to 125 degrees, and the angular segment [F] may be defined as the angles from about 125 to 230 degrees.

The locations of the angular segments may be based on the anatomy of the patient and on the desired anatomical targets. For instance, low-energy segments 230 may be located at positions where low-energy radiation is most useful for scanning, such as where a predetermined or selected anatomical target is in the beam path. For example, for at least some beam paths that pass through the breasts, low-energy segments 230 may be positioned accordingly. Similarly, high-energy segments may be positioned such that high-energy radiation passes through the lungs in order to image the lungs. The angular segments may be of any size and located in any position, and the angular segments also do not need to be contiguous. Further, while the angular segments in FIG. 2A are depicted as running from 0-360 degrees, a scan may not require emission at all 360 degrees. For example, during a scan, radiation may only be emitted for some subset of 360 degrees, such as about 15, 30, 45, 60, 90, 120, 150 or 180 degrees. Angular segments may be defined accordingly based on the total desired angle of the scan. In some examples, a single scan may mean that the radiation source passes through the angular sweep once. In other examples, a single scan may mean that all the emission and detection of radiation occurs within 360 degrees or less around the longitudinal axis of the patient (e.g., the radiation source and detector make no more than one pass around the patient). In other examples, a single sweep may mean that the patient 120 only enters and exits the CT system once.

Figure 2B:
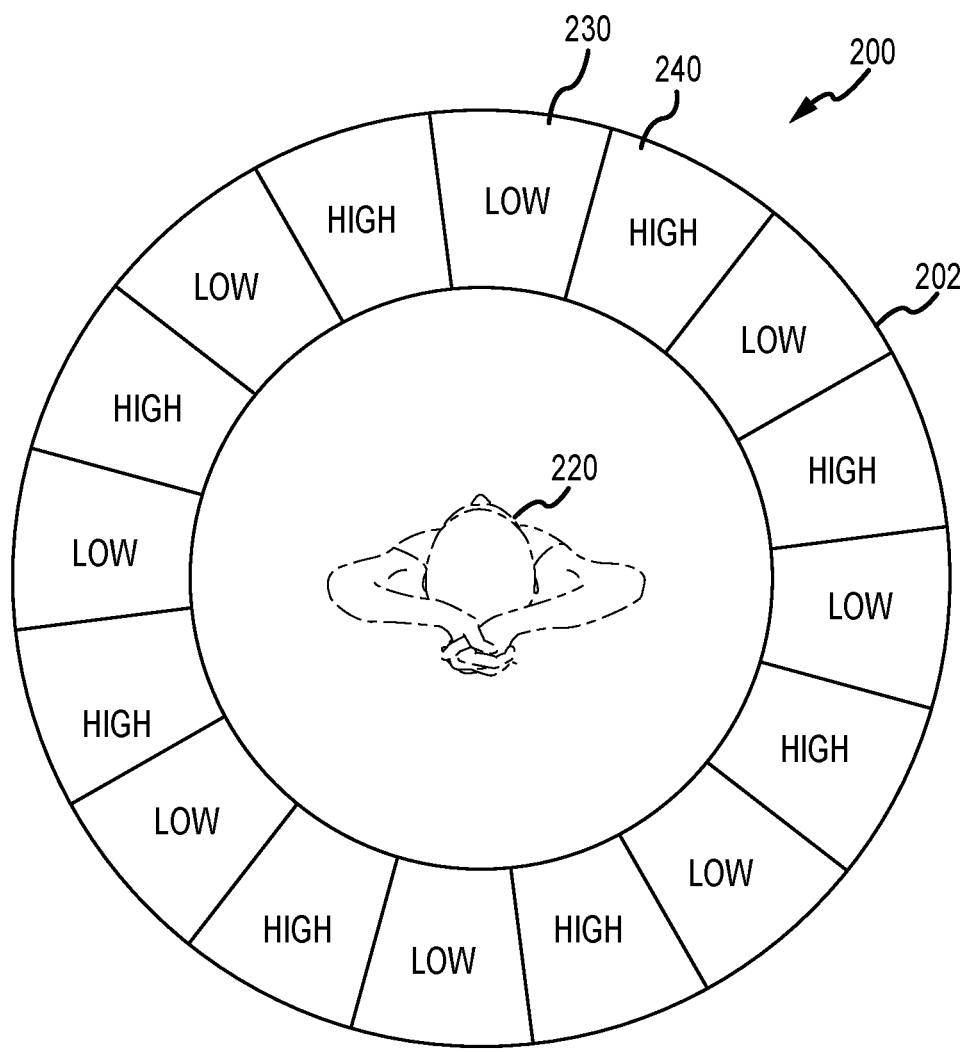
FIG. 2B depicts another view of an example CT system showing example regions of varying radiation emission.

FIG. 2B depicts another view of an example CT system showing example regions of varying radiation emission. The example depicted in FIG. 2B is substantially the same as the example depicted in FIG. 2A with the exception of the layout of the angular segments. In the example depicted in FIG. 2B, the angular segments alternate from low-energy angular segments 230 to high-energy angular segments 240 more rapidly. Further, the low-energy segments 230 and the high-energy angular segments 240 are approximately the same size—about 25 degrees.

Figure 3:
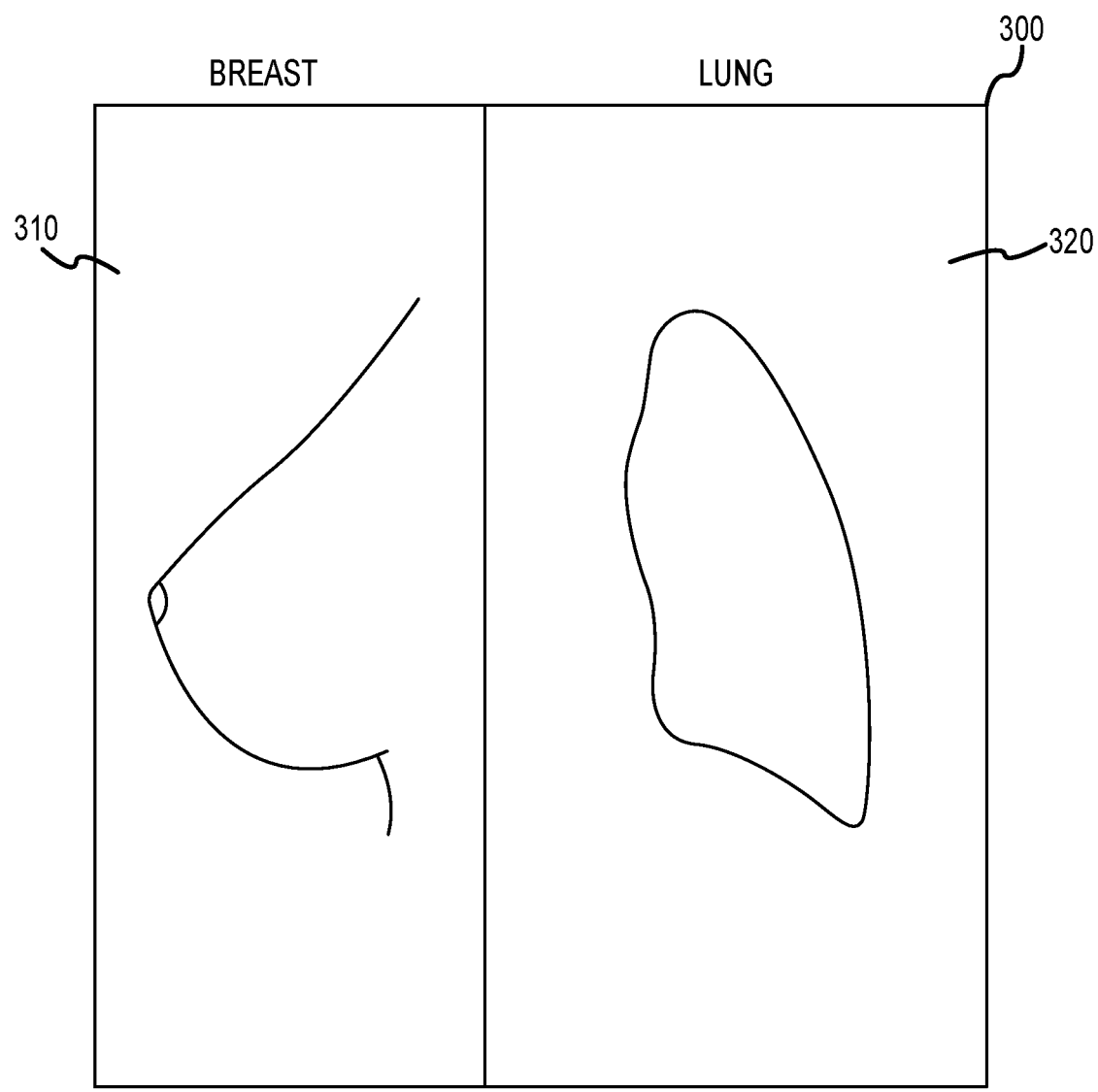
FIG. 3 depicts an example of a display of generated images for two anatomical targets.

FIG. 3 depicts an example of a display 300 of generated images for two anatomical targets. In particular, the two anatomical targets are a breast and a lung of a patient. The display may be of a reconstructed image of the anatomical targets based on the detected radiation during the scan. As depicted, a breast image 310 is provided adjacent to a lung image 320. The images may be of a particular slice of a 3D reconstruction of the anatomical targets. The slice and orientation may be substantially the same for both the anatomical targets. As such, a medical professional reviewing the images may be able to correlate an abnormality in the first anatomical target to an anomaly in the second anatomical target. Correlation or other analysis software may also be utilized in displaying reconstructions of the anatomical targets. The display of the anatomical targets may also be rearranged or otherwise configured in any way to allow the medical professional to be able to correlate one image with another. Multiple slices of each anatomical target may also be displayed concurrently or consecutively. The images may also be 3D images that a user may rotate or otherwise manipulate to view different portions of the reconstructed anatomical target(s). In some examples, both anatomical targets need not be displayed concurrently. The display may also include indicators or markers resulting from computer-aided diagnostic programs.

Figure 4:
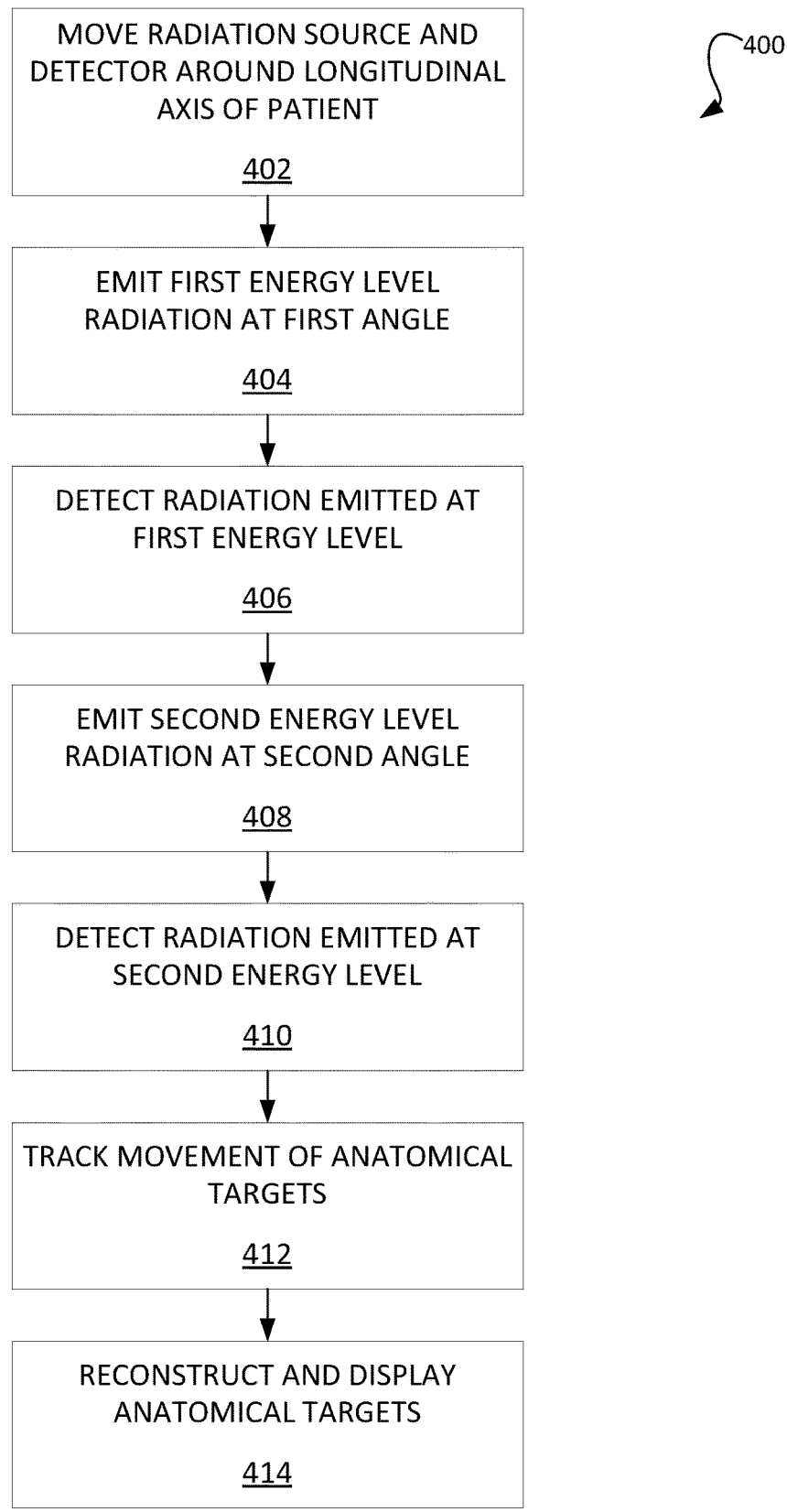
FIG. 4 depicts an example method for imaging multiple anatomical targets of a patient.

FIG. 4 depicts an example method 400 for imaging multiple anatomical targets of a patient. At operation 402, a radiation source and a detector are moved around a longitudinal axis of a patient. For example, a radiation source and a radiation detector may move around an annular housing of a CT system as discussed above. The radiation source and radiation detector may move in a manner that allows them to remain disposed opposite one another. In some examples, based on the size and configuration of the radiation source and detector, only one of the radiation source or the detector may move.

When the radiation source is at a first predetermined angle, or within a range of angles, the radiation source emits radiation a first energy level, at operation 404. For example, as discussed above, when the radiation source is within a particular angular segment, the radiation source emits radiation of a particular energy level corresponding to the angular segment. The energy level corresponding to the first predetermined angle may be a low energy level or a high energy level. In some examples, the radiation may be emitted while the radiation source is moving. In other examples, the radiation source may temporarily stop movement and emit radiation. The radiation source may then resume movement after emission is terminated.

At operation 406, the radiation emitted at the first energy level is detected by a radiation detector. For instance, after the radiation emitted in operation 404 passes through and is attenuated by the patient, the radiation is detected by the detector. Detection may include receiving the radiation and converting the radiation into digital signals that can be used for image processing and reconstruction.

At operation 408, when the radiation source is at second angle or within a second singular range, the radiation source emits radiation at a second energy level. For example, as discussed above, when the radiation source is in another angular segment, the radiation source emits radiation at a second energy level that is different from the first energy level. In some examples, the first energy level may be a low energy level and the second energy level may be a high energy level. In some examples, the first energy level radiation may be radiation produced by applying less than 50 kV across the radiation source and the second energy level radiation may be radiation produced by applying more than 50 kV across the radiation source. In addition, as discussed above, the first and second energy levels may be based on the anatomical targets that are intended to be scanned or imaged. For instance, a first energy may be selected for a breast and a second energy level may be selected for a lung.

At operation 410, the radiation emitted at the second energy level is detected by the detector. Detection of the different radiation levels, or the related processing of the detected data, may also include changing resolution or binning. For example, for detecting the first energy level radiation, a high resolution binning (e.g., 1×1) may be used. For detection of the second energy level radiation, a lower resolution binning (e.g., 4×4) may be used. In general, where the anatomical targets are a breast and a lung, detection and processing of a first energy level radiation may utilize mammography techniques whereas detection and processing of the second energy level radiation may utilize lung cancer x-ray screening techniques.

At operation 412, movement of the anatomical targets is tracked. The movement tracking of operation 412 may be continuously performed during a scan of the patient. Tracking of the movement of the anatomical targets may be done through various mechanisms. For example, where the anatomical target is a breast, one or more radiopaque markers may be attached to the breast, as discussed above. In such an example, the location of the radiopaque markers can be tracked through the radiation data that is detected by the detectors. In other examples, optical devices may be used to track the movement and location of the breast. The heart rate and breathing rate of the patient may also be tracked. The heart and breathing rate may be tracked by heart or breathing monitors. The heart rate and breathing rate may be used to estimate the location of the anatomical target. For instance, with each breath or beat of the heart, the breast may move incrementally. As such, by tracking the heart and breathing rates, inferences can be made about the movement of the breast. Other anatomical targets also move with heartbeats and breaths. For instance, the lung obviously moves with each breath that is taken. The lung may also move incrementally based on heart beats. As such, movement of the lung may also be approximated based on the heart beat and breathing rates.

At operation 414, the anatomical targets are reconstructed based on the detected radiation. The reconstruction may also be further corrected and/or based on the movement data captured in operation 412. For example, the first anatomical target may be reconstructed based on the detected radiation at the first energy level. The reconstruction of the anatomical targets, or a portion thereof, may also be displayed at operation 414. The display of the anatomical targets may be a display similar to that discussed above with reference to FIG. 3. Reconstruction and generation of images may include using any of the techniques discussed in U.S. Pat. No. 8,787,522; U.S. Patent Publication No. 2014/0321607; and U.S. Patent Publication No. 2016/0256125, which are all incorporated by reference herein in their entirety. In some examples, the high resolution component of the detected radiation combined with the low resolution component of the detected radiation effectively renders the resultant image data a high resolution CT image. One strength of the algorithms and techniques is to convolve the high energy low resolution with low energy high resolution image into a single image presentation. By controlling the distribution of dose through switching energy levels, the reconstruction can be targeted to specific region of interest or anatomy of interest, taking advantage of the combined energies or doses and the combined resolution. In some instances, decomposition of resolution may be done in the frequency domain.

Figure 5:
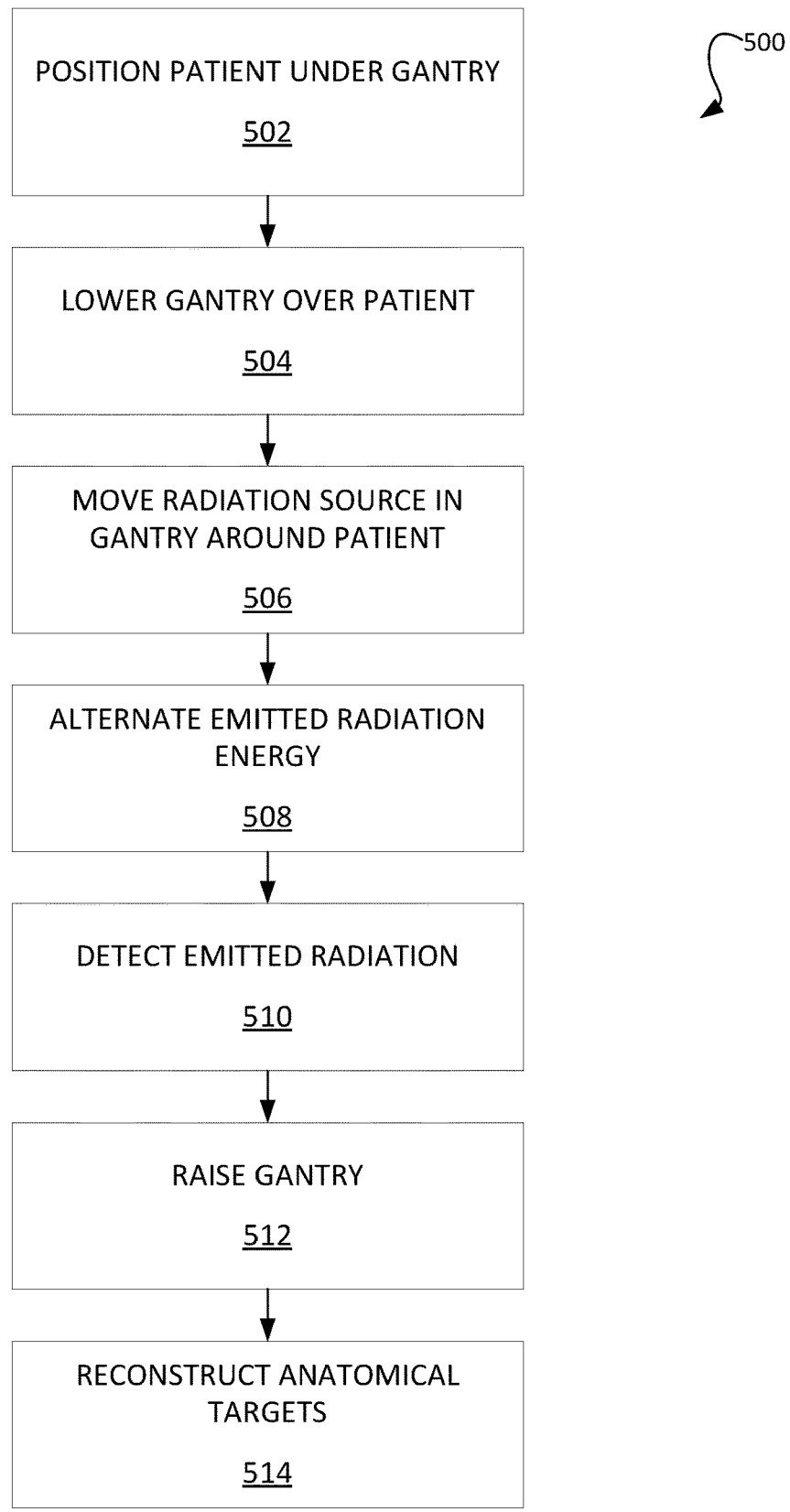
FIG. 5 depicts an example method for imaging multiple anatomical targets of a patient using a standing CT system.

FIG. 5 depicts an example method 500 for imaging multiple anatomical targets of a patient using a standing CT system. At operation 502, a patient is positioned underneath a gantry of the standing CT system. The patient may be positioned under the central aperture of the gantry such that when the gantry is lowered, the patient fits within the aperture. In other examples, a portion of the gantry, such as hinged or sliding portion, may be opened to allow the patient to enter the central aperture of the gantry. One the patient has entered the gantry, the sliding or hinged portion of the gantry is closed. Depending on the anatomical targets intended to be scanned, the arms of the patient may also be positioned so that the arms do not obstruct or interfere with the scan. For example, where the anatomical targets are the breast and the lung, the arms of the patient may be positioned above the head of the patient. Once the patient is properly positioned, the gantry is lowered over the patient at operation 504. As an example, where the gantry includes an annular housing with an aperture, lowering the gantry causes at least a portion of the annular housing to pass over a portion of the patient such that the patient is positioned within the aperture of the annular housing. Repositioning of the patient may be useful once the gantry has been lowered if the patient has moved during the process.

Once the gantry has been lowered and the patient is properly positioned, radiation is emitted from a radiation source in the gantry. The radiation source may also move throughout the gantry as it emits alternating radiation, as discussed above. In such an example, the radiation detector may also move throughout the gantry such that it remains substantially opposite the radiation source. The alternating radiation that is emitted may alternate from low-energy radiation to high-energy radiation and back to low-energy radiation. The location for emission of low-energy and high-energy radiation emission may also be based on an angular location of the radiation source. At operation 510, the radiation is detected after passing through the patient. Detection of the radiation may use any of the techniques discussed above. Once the scan has been completed, the gantry is raised and the patient can exit the standing CT system at operation. In some examples, the gantry may be raised or lowered to perform a scan of another portion of the body. For example, a scan of the torso may first be completed, followed by a scan of the abdomen, and potentially of other portions of the body. The gantry may also move continuously in a vertical direction as radiation is emitted to scan more of the body. Such a scan may be similar to helical or spiral CT scan. At operation 514, the anatomical targets may be reconstructed and displayed in at least the same manners as discussed above.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art. For example, the technology is not limited to scanning breasts and lungs. Rather the technology is useful for scanning any anatomical target. For instance, any two or more anatomical targets may be imaged from a single scan. More efficient screening and diagnostic processes are thus provided by imaging the two or more anatomical targets within a single scan, especially in later stages where cancer may metastasize or otherwise move to other parts of the body.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A method for imaging two or more anatomical portions of a patient, the method comprising:
    moving a radiation source and a detector at least partially around a longitudinal axis of the patient;
    emitting radiation at a first energy level at a first angle around a longitudinal axis of the patient, wherein the first energy level is a predetermined energy level for a first anatomical target, wherein the first anatomical target is a breast;
    detecting the radiation emitted at the first energy level;
    emitting radiation at a second energy level at second angle around the longitudinal axis of the patient, wherein the second energy level is a predetermined energy level for a second anatomical target, wherein the second anatomical target is a lung; and
    detecting the radiation emitted at the second energy level.

2. The method of claim 1, wherein the first energy level is less than the second energy level.

3. The method of claim 1, wherein the energy levels of the radiation emitted from the radiation source are controlled by altering voltage across the radiation source.

4. The method of claim 1, wherein the first energy level corresponds to a voltage of less than 50 kV across the radiation source and the second energy level corresponds to a voltage of 50 kV or greater across the radiation source.

5. The method of claim 1, further comprising reconstructing the first anatomical target from the detected radiation emitted at the first energy level.

6. The method of claim 1, further comprising displaying a representation of the first anatomical target.

7. The method of claim 1, further comprising reconstructing the second anatomical target from the detected radiation emitted at the second energy level.

8. The method of claim 1, further comprising displaying a representation of the second anatomical target.

9. The method of claim 1, further comprising tracking movement of the first anatomical target based on at least one opaque marker placed on the first anatomical target.

10. The method of claim 1, wherein tracking movement of the first anatomical target is based on at least one of heart pulses and breathing rates.

11. The method of claim 1, wherein the radiation source and the detector are housed within an annular housing defining a central aperture for a patient.

12. The method of claim 11, wherein the annular housing is attached to a support structure extending substantially vertically from the ground, wherein the annular housing is configured to move around a patient in a standing position.

13. The method of claim 1, wherein the emission and detection all occurs within a single scan spanning less than or equal to 360 degrees around the longitudinal axis of the patient.

14. A system for imaging two or more anatomical portions of a human body, the system comprising:
    at least one support structure, wherein the support structure extends in an upwards direction from the ground;
    a gantry attached to the at least one support structure and configured to move along the support structure, wherein the gantry comprises an annular housing defining an inner aperture to allow for the annular housing to pass over a patient, wherein the annular housing further comprises:
        a radiation source configured to move through the annular housing around the inner aperture; and
        a radiation detector disposed substantially on an opposite side of the aperture from the radiation source and configured to move through the annular housing to remain substantially on the opposite side of the aperture from the radiation source as the radiation source moves; and
    a control system having at least one processor and memory, wherein the memory stores instructions that when executed by the at least one processor perform a set of operations comprising:
        cause the radiation source to emit radiation at a first energy level for a first angular range around the annular housing, wherein the first energy level is predetermined based on a first anatomical target that is a breast; and
        cause the radiation source to emit radiation at a second energy level for a second angular range around the annular housing, wherein the second energy level is predetermined based on a second anatomical target that is a lung.

15. The system of claim 14, wherein the system further comprises a display screen for displaying a representation of the first anatomical target based on the radiation emitted at the first energy level and a representation of the second anatomical target based on the radiation emitted at the second energy level.

16. The system of claim 14, wherein the first angular range is based on a position of the first anatomical target and the second angular range is based on a position of the second anatomical target.

17. A method for imaging two or more anatomical portions of a patient, the method comprising:
- moving a gantry, having an annular housing with an aperture, down over a patient in a standing position such that the patient is within the aperture of the annular housing;
- moving a radiation source and a detector around the annular housing, such that the radiation source and the detector remain substantially opposite one another;
- while moving the radiation source around the annular housing, alternating radiation emission between a low-energy radiation and a high-energy radiation, wherein the low-energy radiation is predetermined based on a first anatomical target that is a breast and the high-energy radiation is based on a second anatomical target that is a lung;
- detecting the emitted radiation; and
- based on the emitted radiation, reconstructing the first anatomical target and the second anatomical target.

* * * * *